US00PP27709P3

(12) United States Plant Patent
Vorsa et al.

(10) Patent No.: US PP27,709 P3
(45) Date of Patent: Feb. 28, 2017

(54) CRANBERRY VARIETY NAMED 'CNJ99-52-15'

(50) Latin Name: ***Vaccinium macrocarpon* Ait.**
Varietal Denomination: CNJ99-52-15

(71) Applicant: Rutgers, The State University of New Jersey, New Brunswick, NJ (US)

(72) Inventors: Nicholi Vorsa, Atco, NJ (US); Jennifer Johnson-Cicalese, Medford, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 152 days.

(21) Appl. No.: 14/544,114

(22) Filed: Nov. 24, 2014

(65) Prior Publication Data
US 2016/0150693 P1 May 26, 2016

(51) Int. Cl.
*A01H 5/08* (2006.01)

(52) U.S. Cl.
USPC ..... Plt./156

(58) Field of Classification Search
USPC ..... Plt./156
See application file for complete search history.

*Primary Examiner* — Keith Robinson
(74) *Attorney, Agent, or Firm* — Klarquist Sparkman, LLP; Sheree Lynn Rybak

(57) ABSTRACT

A new cranberry variety distinguished by early mid-season ripening period, precocious cropping, high productivity, and moderate-to-high fruit anthocyanin development, as compared to the currently cultivated commercial varieties.

1 Drawing Sheet

Latin name of the genus and species of the plant claimed: *Vaccinium macrocarpon* Ait.

Variety denomination: 'CNJ99-52-15'.

BACKGROUND

The American cranberry (*Vaccinium macrocarpon* Ait.) is a temperate, woody perennial plant species native to North America. The United States is the largest producer, with Wisconsin and Massachusetts representing the majority of cranberry acreage and production, followed by New Jersey, Oregon and Washington. Varieties that currently are commercially cultivated include selections from native populations, and first and second breeding and selection cycle hybrids. Significant acreage is still devoted to varieties that were selected from native cranberry populations from as far back as 1843, including 'Ben Lear' (unpatented), 'Early Black' (unpatented), 'Howes' (unpatented), 'Lemunyon' (unpatented), 'McFarlin' (unpatented) and 'Searles' (unpatented). First breeding and selection hybrid varieties were developed by the United States Department of Agriculture, in cooperation with state Agricultural Experiment Stations in the 1940's, and the program released a series of unpatented varieties in the 1950's including the most widely grown cultivar 'Stevens', which was selected from original test plots in Pemberton, N.J. During the 2000-2010 decade, patented and unpatented varieties from a second breeding and selection cycles have been introduced and grown commercially.

The bulk of cranberry production is for the processed market, including both juice and 'sweetened dried cranberry' (SDC) fruit products, where fruit having specific total anthocyanin content (TAcy) ranges are desired. For SDC processors, certain fruit quality criteria are desired, including larger fruit size (>1.5 g/berry), a round fruit shape, mid-range TAcy, moderate to high titratable acidity (TA, 2.3-2.5 citric acid equivalents), and high soluble solids (Brix). Another important cranberry market is fresh fruit, where berry appearance and storage life are essential traits. For economic sustainability, cranberry growers require varieties with consistent high productivity, acceptable levels of disease resistance to both fruit and vine diseases, and desired season of harvest. In cranberry, varietal variation for crop productivity is a function of inherent differences among varieties for traits such as stolon vigor, upright (vertical reproductive shoots) density, inflorescence bud production, fruit set and fruit size. Varieties with high stolon vigor will establish more rapidly and reduce the number of years required to achieve maximal production. However, after stolon colonization of the bed, varieties must transition to optimal sexual reproduction mode, and optimal upright density, to achieve high crop production. Cranberry inflorescence bud primordia are set on uprights during the completion of the fruit development period and overwinter in a dormant state, before resuming growth the subsequent spring. Thus, the crop load of a given year, may impact the subsequent year's cropping, contributing to the pronounced biennial bearing habit common to many varieties. Productivity is also subject to environmental effects, e.g., heat and light intensity stresses, cold (frost) stress, water stress (drought and excess), disease, insects, certain pesticides, etc.

TAcy content is a fruit quality component of cranberry, usually having a minimum acceptable value. TAcy is typically measured as mg of total anthocyanin per 100 g fruit fresh weight, using a standard spectrophotometric method (@ 520 nm absorbance). For SDC products, there is a desired range, minimum and maximum, for TAcy, typically 20-40 mg total anthocyanins/100 g fresh weight. Earlier ripening varieties, which typically have higher TAcy, allow for earlier harvesting of a crop. Anthocyanins are largely located in the fruit epidermis, which results in a generally larger fruit having lower TAcy. The Rutgers University cranberry breeding program quantitatively measured TAcy along with mean fruit size, and selected progeny with large fruit size and high TAcy levels.

New Jersey uniquely offers an ideal environment for cranberry breeding because of the climate, soils and water. Of all the cranberry production areas in North America, New Jersey conditions subject the cranberry to the highest disease pressure and heat stresses. The plant and developing fruit must tolerate high heat stress, and fruit and vegetative diseases during the growing season. Over 15 pathogens are known to incite cranberry fruit rot in New Jersey, and the fruit is also subject to heat scald and physiological breakdown. Thus, selection under New Jersey conditions offers the opportunity to identify varieties with higher resistance to disease, scald, and heat stress.

The Rutgers University cranberry breeding program, in Chatsworth, N.J., was initiated in 1985 to take advantage of this unique selection pressure. The program's methods were designed to duplicate, as much as possible, the environment of a commercial bed. Breeding plots of 1.5×1.5 m are established with multiple plants and allowed to 'fill in' to form a dense canopy. Two to three years after planting, yield of a given plot is evaluated over a three year minimum to provide for biennial bearing assessment. Parental selection was based on parental field phenotypic performance, and parental progeny performance of cross combinations based on the objectives of enhancing traits and/or combining the most desirable traits from both parents into one genotype, i.e., variety. Traits being evaluated in this breeding program include yield, ripening season, fruit rot susceptibility/resistance, storage life, scald susceptibility, stolon and upright vigor, total anthocyanin content (TAcy), soluble solids (Brix), titratable acidity, and berry shape and appearance.

SUMMARY

The present disclosure provides a new and distinctive American cranberry variety, 'CNJ99-52-15', for the processed cranberry market, having a high crop yield potential, a mid-season ripening period, a round to ovate berry, and a propensity for precocious cropping. 'CNJ99-52-15' is especially suited to an 'oceanic climate'; typical of middle latitude west coasts of many continents, which generally have warm (maximum temperatures <22° C.) summers and not excessively cold winters (minimum temperatures >−3° C.).

The variety, 'CNJ99-52-15', described herein, resulted from a 1999 cross between the variety '#35' (unpatented) as the seed parent, with 'NJS98-34' (unpatented) as the pollen parent. 'NJS98-34' is a selection from a 'Franklin×Ben Lear' cross and '#35' is from a 'Howes×Searles' cross. '#35' was originally selected from a previous USDA/NJAES cranberry breeding program (Dana, Minn. Cranberry cultivar list (*Vaccinium macrocarpon*). Fruit Varieties J 37:88-95, 1983). 'CNJ99-52-15' was originally selected in 2007 from among 112 siblings of this cross established in mature solid stand plots, in a breeding trial containing 250 progeny in Chatsworth, N.J. for its very high yield potential, mid-season ripening, large widely-ovate to round berry and uniform fruit color. In 2007, 'CNJ99-52-15' was selected for testing in advanced replicated selection trials in Oregon, Washington and Wisconsin. 'CNJ99-52-15' exhibits precocious cropping during bed establishment with consistently high yield crops and early to mid-season ripening. Although originally selected under New Jersey's environmental stresses, 'CNJ99-52-15' is especially suited to an 'oceanic climate'.

The 'CNJ99-52-15' variety is distinguished from other cranberry varieties in having precocious high yield fruit production, with early-midseason ripening. Fruit are moderate to large, with a widely ovate to nearly round fruit shape. 'CNJ99-52-15' can be distinguished from its seed parent '#35' by its earlier bloom, earlier ripening and higher Tacy, from its pollen parent 'NJS98-34' by consistently higher yield, and from both of its parents by its precocious yielding habit.

'CNJ99-52-15' has been asexually reproduced by cuttings in Chatsworth, N.J. since 2007. Over that period, no evidence of 'off-types' of 'CNJ99-52-15' has been observed. 'CNJ99-52-15' appears genetically stable and reproduces true to type in successive generations of asexual reproduction.

The following description describes the cranberry variety 'CNJ99-52-15'. The original plant and vegetative propagules were observed in a cranberry bed maintained with standard management practices for commercial cranberry production in Chatsworth, Burlington County, N.J. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart (2001).

BRIEF DESCRIPTION OF THE DRAWING

FIG. 1 shows representative fruit of 'CNJ99-52-15' displaying the variation in fruit size, shape and color; harvested and photographed September 2014 in Chatsworth, N.J.

The colors of an illustration of this type may vary with lighting and other conditions, therefore, color characteristics of this new variety should be determined with reference to the observations described herein, rather than from these illustrations alone.

DETAILED BOTANICAL DESCRIPTION

The following detailed description of the 'CNJ99-52-15' variety is based on observations of plants growing in the field in Chatsworth, N.J. The characteristics of the variety were compared to 'Stevens' and 'Ben Lear' (both unpatented), two widely cultivated cranberry varieties. The observed plantings were 3-6 years of age.

Scientific name: *Vaccinium macrocarpon* Ait.

Parentage:

*Seed parent*.—Variety '#35' (derived from a 'Searles'× 'Howes' cross).

*Pollen parent*.—Variety 'NJS98-34' (an advanced selection from a 'Franklin×Ben Lear' cross).

Plant:

*Vigor*.—General observations of 'CNJ99-52-15' plantings indicate above average plant vigor.

*Growth habit*.—Trailing shrub with very slender stems.

*Upright length*.—8.8 (mean of 30 uprights).

*Stem diameter*.—1.25 mm at base of current year's growth (mean of 30 stems).

*Internodes*.—Internode length was 8.6 mm on 1-year old runners (mean of 15 runners).

*Productivity*.—In established test plots in Chatsworth, N.J., 'CNJ99-52-15' yields were greater than 'Stevens' and 'Ben Lear'.

*Hardiness*.—Zones 4-7 (from USDA Misc. Publ. 814).

*Disease resistance*.—No disease resistance data available for foliar or root pathogens.

Leaves: The length, width and other measurements were obtained from observations of 30 typical fully developed leaves in September 2013. Color was determined on actively growing plants.

*Texture*.—Coriaceous (leathery) on upper and lower surfaces.

*Length*.—Mean of 10.0 mm, with a maximum 12.7 mm.

*Width*.—Mean of 3.9 mm, with a maximum of 5.2 mm.

*Shape*.—Ovate (2.5:1 ratio, length:width).

*Apex shape*.—Rounded.

*Base shape*.—Rounded, nearly sessile.

*Margin*.—Entire, slightly revolute.

*Leaf color*.—Upper leaf surface color ranges from bright green (143C, green group) in new growth to deep green in mature leaves (139A to 137C, green group).

*Pubescence*.—Non-glandular trichomes found along leaf margins towards leaf apex.

Flowers: Observations are from 10 typical flowers collected from test plots in Chatsworth, NJ, Jun. 18, 2014.

*Size and shape*.—Slender, nodding flowers on erect pedicels and in clusters of typically 3-6 flowers; corolla long-conic in bud, petals fully reflexed and divided nearly to the base when open.

*Unopened corolla*.—Approx. 9 mm long and deep pink in color (68D, red-purple group). Opened flower: measuring about 10 mm across, 4 petals per flower.

*Petals*.—Narrow and revolute in shape, 9.5 mm by 2.7 mm; pale pink in color (69C, red-purple group); glabrous texture on upper and lower surfaces.

*Pedicel*.—19.2 mm in length by 0.75 mm in diameter with a pubescent texture; the color ranges from pale green (195D, greyed green group) to pink (red group 48C).

*Bloom season*.—Bloom typically begins in early June and continues throughout the month. Peak bloom for 'CNJ99-52-15' is earlier than '#35' and slightly later than 'NJS98-23' (U.S. Plant Pat. No. 18,252), typically June 7-14 in New Jersey.

*Mean number of flowers per upright*.—4.9.

Fruit: Observations are from 30 typical fruit harvested from test plots in Chatsworth, N.J., Sep. 18, 2013 and Oct. 5, 2014.

*Shape*.—Widely ovate to very widely ovate, with rounded to slightly oblique pedicle end (FIG. 1); fruit length to width ratio of 1:1.1 to 1:1.35; calyx end slightly rounded to slightly flat with unpronounced calyx lobes (FIG. 1).

*Size*.—In NJ, average size was 1.8-2.0 cm long (pedicel to calyx end) and 1.5-1.8 cm wide.

*Skin*.—Shiny, waxy bloom around calyx (FIG. 1), otherwise with slight scattered waxy bloom.

*Color*.—Ranged from 46C (red group) for the lightest berries, 185A (greyed-purple group) for medium berries, to N186C (greyed-purple group) for the darkest (harvested fall 2014).

*Stem pit*.—Small and slightly indented, average of 1.8 mm in diameter.

*Average weight*.—50 berry samples collected from test plots in 2007-2010 had yearly mean berry weights ranging from 2.0 to 2.4 g, with a maximum berry weight of 3.7 g.

*Fruit firmness*.—Firm.

*Number of seeds*.—Mean seed number per fruit was 14; a maximum of 30 seeds/fruit was observed.

Seeds: Observations are from 10 seeds extracted from typical fruit harvested from test plots in Warrens, Wis., September 2015.

*Size*.—2.48 mm in length by 1.38 mm in width.

*Shape*.—An oval that is slightly triangular and with elongated pointed ends.

*Color*.—165b (greyed orange group, RHS).

*Texture*.—Striated.

Fruit chemistry: 100 g samples of fruit were harvested each year from test plots in Chatsworth, N.J. and evaluated for fruit chemistry. 'CNJ99-52-15' mean TAcy values were less than 'Ben Lear' and greater than 'Stevens' in September. 'CNJ99-52-15' had titratable acidity values of 2.2% to 2.7% and Brix values of 7.7-9.2%.

Fruit production: 'CNJ99-52-15' season is early mid-season, ripening slightly after early varieties, e.g., 'Ben Lear', 'NJS98-23', and but before later season varieties, 'Stevens' and 'CNJ97-105-4' (U.S. Plant Pat. No. 19,434).

Usage: Most suitable for processed cranberry products.

Disease resistance: In New Jersey, where disease pressure is severe, 'CNJ99-52-15' has moderate susceptibility to fruit rot (a disease complex of over 15 pathogens, primarily *Colletotrichum gloeosporioides, Physalospora vaccinii, Phyllosticta vaccinii, Phomopsis vaccinii*, and *Coleophoma empetri*).

We claim:

1. A new and distinct variety of cranberry plant, substantially as herein shown and described.

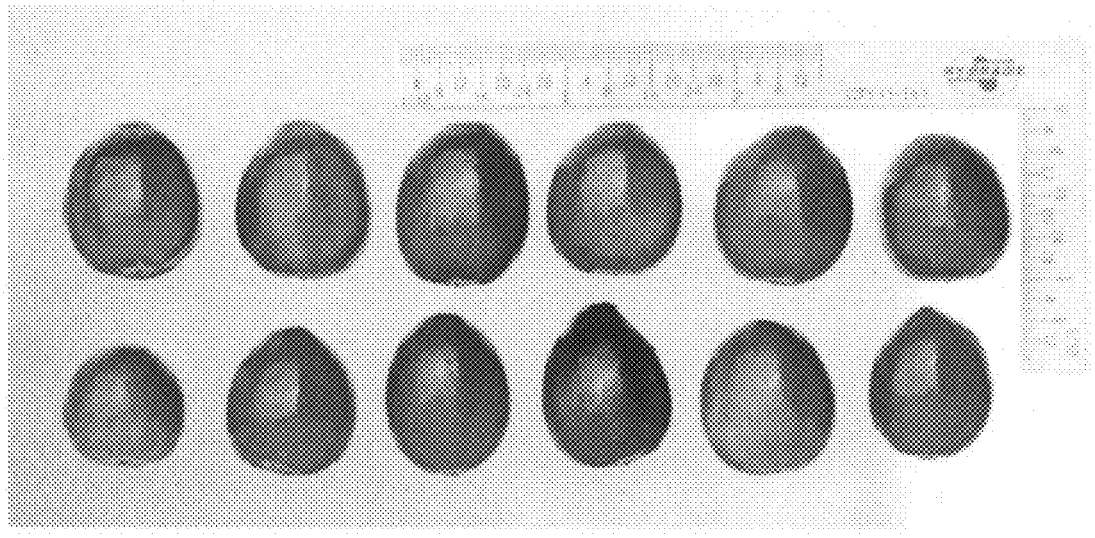

* * * * *